Aug. 10, 1954 J. D. BROWNELL Plant Pat. 1,295
ROSE PLANT
Filed Jan. 9, 1952
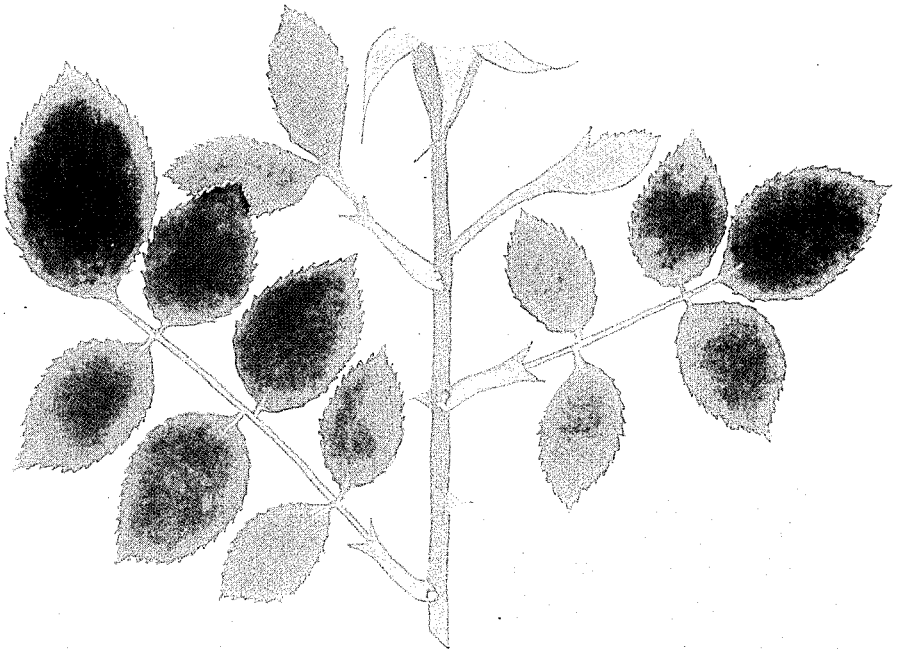
Josephine D. Brownell INVENTOR.

Patented Aug. 10, 1954

Plant Pat. 1,295

UNITED STATES PATENT OFFICE 1,295

ROSE PLANT

Josephine D. Brownell, Little Compton, R. I.

Application January 9, 1952, Serial No. 265,626

1 Claim. (Cl. 47—61)

My invention relates to rose plants and especially to a new, original and distinct variety of the class known commercially as "hybrid teas" and is a variant in that class, being a *Rosa wichuraiana* hybrid tea hybrid, in combination with cane growth usually common to climbing roses only, except the canes of my new rose usually bear terminal flowers and recurrent blooms on branches therefrom, often the same year that the canes grow; produced by me and under my direction in the breeding grounds of my research gardens in Little Compton, Rhode Island, by selection of variety variations and by cross pollenation, which can be and has been asexually reproduced.

My new rose is new as to the following characteristics and especially as to their joint association with the characteristics inherited from *Rosa wichuraiana,* of hardiness, or immunity from serious injury on account of cold temperatures prevailing in certain parts of the northern United States:

The crimson to magenta shades (ordinary dictionary definitions) of its petals, in combination with the unique brilliance thereof and their tendency to hold these colors under exposure;

The novelty and variation within certain definite limits of the form of the bloom, its character of holding that form for a long time, and the petallage of the flowers;

Its character of fragrance;

Its unusual abundance of flowers, notable after early bloom time and until frost;

The intensity of its remontant and everblooming or reblooming character;

Its character of ascending in height by recurrent branching and progressively longer stems from the base in some instances long enough to be classified as canes;

The character of producing many seven leafleted leaves; which character seldom has obtained on hybrid teas not having *Rosa wichuraiana* ancestry, but frequently obtains on flower stems of descendants of *Rosa wichuraiana* of the dwarf reblooming type;

Under the natural conditions of exposure where this rose was grown it has shown some resistance to black-spot.

In the accompanying drawing forming a part of this specification I have shown my new rose in its natural colors, that is, as near as is possible to do so artificially.

My new rose is otherwise described as follows:

*Essential information*

*Type.*—Hybrid tea, *Rosa wichuraiana* hybrid, climber, for garden display, cut flower and forcing or growing under glass.

*Class.*—Hybrid tea crossed with *Rosa wichuraiana,* further restricted by originator to include only those varieties that can survive moderately low sub-zero temperatures.

*Breeding.*—This variety was produced and bred by me and under my direction by propagation, selection and cross pollenation.

It came into being as a seedling grown from a seed borne on a plant of an unnamed seedling not patented and the pollen parent was "Queen o' the Lakes" Plant Patent No. 1,003.

The pollenation that fertilized the seed that grew into my new rose, as well as the two previous pollenations that produced its two parents, were directed by me and were performed by emasculating flowers and placing thereon a bag protecting from self and foreign pollen. These bags were later removed and the flowers were hand pollenated with a camel's hair brush and the bags immediately replaced. The date of the pollenation of my new rose was July 11, 1948.[1] The seed was planted for me and under my direction on December 22, 1948, and the date of the first flower was July 25, 1949.

I have since made and directed extensive propagations and tests of this plant and flower.

Plants of this variety budded from this seedling on to *Rosa multiflora* root stock, have after being exposed to moderate sub-zero temperatures, survived and bloomed normally the following season in the hybrid tea manner. The variety has been propagated by budding at Little Compton, Rhode Island, in the months of July and August 1950 and the characters have successively reproduced, true to the original seedling.

*Flower*

*Habit.*—It blooms out of doors in Little Compton, beginning about three days prior to the average beginning time of commercial hybrid

[1] This and other dates herein are approximate.

teas and continues relative to growth of the plant until frost.

*Flowers borne.*—Often one, frequently two or three and occasionally more on each stem, in the usual hybrid tea type of cluster, and frequently on climber canes as they grow. Such canes terminate in one or more blooms or clusters of blooms; and later in the season branches frequently grow therefrom with terminal flowers.

All of the foregoing bloom expression usually obtains the first year after budding on maidens and on two year old plants the first growing season after being transplanted.

The routine performance thereof is usually as follows. The plant first blooms like a hybrid tea, followed by cane growths in length from about five to six feet, later more in length terminating in blooms. The hybrid tea growth continues to grow rebloom stems in the hybrid tea manner until frost, also similar stems from the cane growths.

The pedicels and peduncles are medium in diameter and medium in length, erect, stiff, almost smooth, free from large prickles and bristles. Stems are long, medium to small in diameter, and notably stiff and rigid.

*Quantity of bloom.*—Free, being cumulative in quantity from year to year as the plant increases in size, flowering through the summer and fall.

*Fragrance.*—Distinctive, pleasing China tea in combination with that of *Rosa wichuraiana,* under favorable environment.

*Bud.*—Neck normal as described, opens well, being little to not at all affected by hot or wet weather or both, as to color and form, except at very high temperatures the color is less intense and the form of the petals is less recurled.

Before the calyx breaks the size is medium, form moderately high pointed, the sepals are usually normal and regular, tapering to lanceolate at the apex, some foliaceous appendages, turning back nearly perpendicular to the pedicel as the bud opens, usually no spurs on sides.

Color of the bud as the calyx opens, both sides of petals Crimson at 22/1; color reference to English Horticultural Color Chart.[2]

*Bloom.*—Color softens slowly to Rose Bengal at 25/2 and later to Magenta at 27/2.

Color slightly variable dependent upon quality of sun or other light.

The flower usually varies in size between four and five inches in diameter when fully open, petals average 40 to 45, frequently some smaller petals and petaloids in the center, variable in number.

The flower opens moderately pointed and high centered, informal, with display of stamens and pistils. The petals are variable from obovate to ovate to irregular and formal as to arrangement and recurl, and edges of the smaller petals occasionally notably irregular, and notably recurled. Texture is medium to thick; both sides brilliant. The time of opening under favorable conditions is about three days.

The petals are substantial and after about five days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

*Reproductive organs.*—Stamens, quantity variable, medium long, of slightly uneven length.

[2] Color references to same unless otherwise indicated.

Anthers, nearly Marigold Orange at 11/3. Filaments, nearly Tangerine Orange at 9/3.

Pistils are several of nearly even length, averaging about one-half inch long.

Sepals are persistent and break off easily.

*Plant*

*Foliage.*—Is abundant, of compound leaves of three to five leaflets near the flower, five leaflets lower down the stem and frequently seven leaflets in the middle of the stems and canes and nearer the base. Often with short narrow leafy formations variously positioned near the flower as shown. Size of leaflets medium. Form of leaflets usually ovate with apex moderately acute, base rounded to slightly pointed in some instances with the circumference on one side of the petiolule out of alignment with the other side by about one-sixteenth of an inch or less, margins with slightly irregular small pointed serrations, petiolules short.

The leaflets average in width about one-half to two-thirds of their length.

Color of leaflets on the upper surface is slightly variable from Scheeles Green at 860, irregularly shaded with Spinach Green at 0960/1, with reverse side nearly Asphodel Green frequently overlaid with trace of Dahlia Carmine, the last two color references are to Robert Ridgway Color Standards.

The rachises are medium, moderately narrow to slender, upper side smooth except some very short hairs on edge. Under side moderately smooth, usually three to five short prickles.

Stipules are long, averaging about one inch long or a little more, with sharp points, the upper edges of which normally form an angle of about 90 degrees.

*Growth.*—As maidens and as first year planted, it grows hybrid tea type of stems terminating in blooms as freely as the average hybrid tea variety, these branch and bloom in the usual hybrid tea manner. Later in the season under normal conditions the plant grows stems or cane lengths from about three to five feet in length that grow blooms at their terminal ends as they mature the year that they grow.

Later in the same year or in the following year the cane growth referred to develops cane branches three to five feet long that similarly bloom and branch; and in addition thereto cane growth develops from the base usually five to ten feet long and sometimes longer and similarly blooms and branches similar cane growth that similarly blooms.

The hybrid tea stem growth continues in combination with cane growth. Hybrid tea bloom growth develops from cane growth and vice versa.

The canes seek to grow at an angle of about 90 degrees from the horizontal.

The hybrid tea growth can usually be distinguished from cane growth by the diameters thereof.

Color of mature stems is Scheeles Green at 860/3, shading variously lighter and also occasionally with slight overlay of Spinel Red at oo23/1 variable in intensity, usually more pronounced on the sunny side.

Prickles, several, frequently two to four between leaves, averaging in length about one-quarter to one-third inch, shading from Crimson at 22 to lighter at the base, turning lighter throughout and later to nearly colorless.

*Winter resistance.*—A notable characteristic of this new rose is the resistance to moderate sub-zero temperatures in combination with its hybrid tea character, its climbing habit and its *Rosa wichuraiana* ancestry. The word "temperature" herein refers to the Fahrenheit scale.

*Comparisons.*—The variety most nearly resembling my new rose is New Dawn, Plant Patent No. 1, which lacks some of the hybrid tea type of rebloom expressed by my new rose.

The color of my new rose is Crimson as compared with New Dawn which is shell pink, ordinary dictionary definition; also, my new rose has a different fragrance.

I claim:

The new and distinct variety of rose plant as described and illustrated, characterized by its color pattern, fragrance, and form of its blooms produced as hybrid teas on hybrid tea type of stems and at the terminal end of canes that bloom the same season in which the canes grow; also, by the *Wichuraiana,* hybrid tea, and ever-blooming climber characteristics, substantially as described.

References Cited in the file of this patent

Bailey, Standard Cyclopedia of Horticulture, vol. 3, p. 3001 (1943).